United States Patent
Otsuka

(10) Patent No.: US 10,054,435 B2
(45) Date of Patent: Aug. 21, 2018

(54) MEDIUM TEXTURE DETECTION DEVICE

(71) Applicant: SEIKO EPSON CORPORATION, Tokyo (JP)

(72) Inventor: Shuji Otsuka, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 15/250,729

(22) Filed: Aug. 29, 2016

(65) Prior Publication Data

US 2017/0059312 A1 Mar. 2, 2017

(30) Foreign Application Priority Data

Sep. 1, 2015 (JP) ................................. 2015-171825

(51) Int. Cl.
*G01B 11/30* (2006.01)
*G01N 21/47* (2006.01)

(52) U.S. Cl.
CPC ....... *G01B 11/303* (2013.01); *G01N 21/4738* (2013.01)

(58) Field of Classification Search
CPC .......................... G01B 11/303; G01N 21/4738
See application file for complete search history.

(56) References Cited

U.S. PATENT DOCUMENTS

| | | | | |
|---|---|---|---|---|
| 4,937,637 A | * | 6/1990 | Magistro | G01N 21/474 356/73 |
| 5,764,874 A | * | 6/1998 | White | G01N 21/8806 355/67 |
| 2010/0277748 A1 | * | 11/2010 | Potapenko | G01B 11/026 356/623 |
| 2014/0320916 A1 | * | 10/2014 | Kato | H04N 1/6044 358/1.15 |

FOREIGN PATENT DOCUMENTS

| JP | 2013-231658 | 11/2013 |
|---|---|---|
| JP | 2017-044511 A | 3/2017 |

OTHER PUBLICATIONS

HP Design jet Z6100-series Printers: Optical Media Advance Sensor, (8 pages), Mar. 2007.
Atsushi Takaura, Ricoh Technical Report No. 39, Development of Laser Speckle-Based Displacement Sensor with High Accuracy, (30 pages), Jan. 2014.
Nakamura Yukito, The Development of High Response Speckle Velocimeter, (26 pages), Konica Technical Report, vol. 4, Jan. 1991.
Haruna Masamitsu, Osaka University, Optical Coherence Tomography, (OCT), (25 pages), Medical Photonics, No. 1.

* cited by examiner

*Primary Examiner* — Hugh H Maupin
(74) *Attorney, Agent, or Firm* — Workman Nydegger

(57) ABSTRACT

A medium texture detection device includes: a radiation optical system that radiates non-coherent light to a sheet-shaped medium which is being transported; and a light reception optical system that receives diffused/reflected light of the non-coherent light from the medium. A surface of the medium has a basic structure for making a change in an intensity of the diffused/reflected light according to a position of the medium in a transport direction of the medium. A visual field of the light reception optical system is set to be equal to or greater than $\frac{1}{10}$ times and equal to or less than 4 times of a size of the basic structure.

4 Claims, 10 Drawing Sheets

$$S(x0) = \int_{x0}^{x0+xv} R(x)dx$$

MEDIUM TEXTURE DETECTION DEVICE

BACKGROUND

1. Technical Field

The present invention relates to a medium texture detection device.

2. Related Art

In printing apparatuses, a scheme of analyzing image data obtained by imaging a texture state such as unevenness of a surface of a sheet-shaped medium which is being transported and detecting a displacement amount (transport amount) of the medium (which is also referred to as a "real-image photography scheme"), as disclosed in, for example, JP-A-2013-231658, is known as a configuration for precisely transporting a sheet-shaped medium (a sheet or a film).

In the real-image photography scheme of JP-A-2013-231658, there is a problem that it is difficult to accelerate an imaging repetition speed. Further, the problem becomes evident as the transport speed is further accelerated. As one example of the resolutions to the problem, a method of widening a one-time imaged area and causing a captured image to have a high definition can be considered. In order to realize this method, however, there is a problem that the sizes of an imaging system device and an optical system device are increased and cost is increased as well. Even when a given transport speed is accelerated in a configuration for widening an imaged area and causing a captured image to have a high definition, it is necessary to increase the size and cost of a new apparatus in a case in which the transport speed is further accelerated. Therefore, there is a limit to the widening of the imaged area and the high definition of the captured image. For this reason, it is preferable to further improve a configuration for detecting a texture state such as unevenness of a surface of a sheet-shaped medium (a sheet or a film).

SUMMARY

The invention can be realized in the following aspects or application examples.

(1) According to an aspect of the invention, a medium texture detection device is provided. The medium texture detection device includes: a radiation optical system that radiates non-coherent light to a sheet-shaped medium which is being transported; and a light reception optical system that receives diffused/reflected light of the non-coherent light from the medium. A surface of the medium has a basic structure for making a change in an intensity of the diffused/reflected light according to a position of the medium in a transport direction of the medium. A visual field of the light reception optical system is set to be equal to or greater than $\frac{1}{10}$ times and equal to or less than 4 times of a size of the basic structure.

According to the aspect of the invention, it is possible to resolve the problem of the increase in the size and cost of the imaging system device and the optical system device described in the related art. Further, a change in a texture state of a surface of a medium according to the position of the medium can be detected as a change in the intensity of the diffused/reflected light at a high speed with a simpler structure than in the related art.

(2) In the medium texture detection device according to the aspect of the invention, the size of the basic structure may be a space period indicating a space frequency component that has a maximum real part among space frequency components included in the change in the intensity of the diffused/reflected light.

According to the aspect of the invention, the size of the basic structure of the medium can easily be set. Therefore, the visual field of the light reception optical system can easily be set to a size appropriate for detecting the change in the texture state of the surface of the medium according to the position of the medium as the change in the intensity of the diffused/reflected light.

(3) In the medium texture detection device according to the aspect of the invention, the non-coherent light may be light with a wavelength of an infrared region.

According to the aspect of the invention, it is possible to easily detect the change in the texture state of the surface of the medium according to the position of the medium as the change in the intensity of the diffused/reflected light more than the visible light.

(4) In the medium texture detection device according to the aspect of the invention, the radiation optical system may include a light source that emits the non-coherent light, and a light-guiding unit that guides the non-coherent light to the medium. The light reception optical system may include an optical fiber that receives the diffused/reflected light from the medium through an incidence surface which is one end surface as a light reception surface and exits the diffused/reflected light from an exit surface which is the other end surface, a photosensor that receives the diffused/reflected light emitted from the exit surface and outputs an electric signal according to an intensity of the received diffused/reflected light, and a condensing lens that condenses the diffused/reflected light emitted from the exit surface of the optical fiber toward the photosensor.

According to the aspect of the invention, it is possible to easily configure the radiation optical system and the light reception optical system detecting the change in the texture state of the surface of the medium according to the position of the medium as the change in the intensity of the diffused/reflected light.

The invention can be realized in various forms. For example, the invention can be realized in various forms such as various apparatuses using a kind-of-medium detection device, a medium speed detection device, or the like, as well as the medium texture detection device.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

Figure 1:
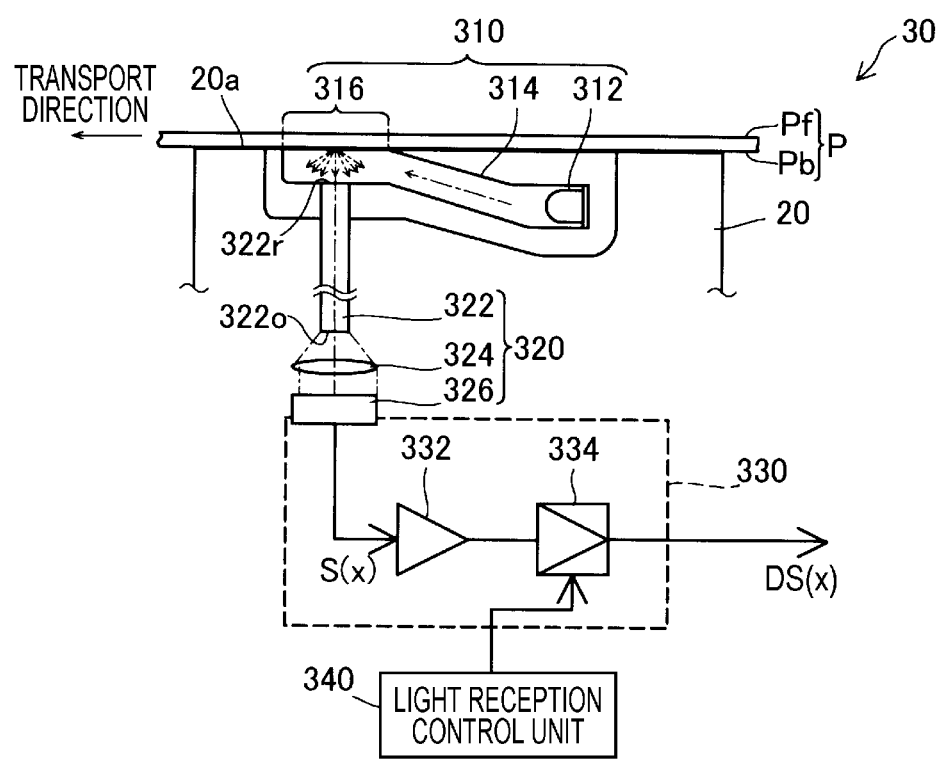
FIG. 1 is a schematic diagram illustrating the configuration of a medium texture detection device according to a first embodiment.

FIG. 1 is a schematic diagram illustrating the configuration of a medium texture detection device 30 according to a first embodiment of the invention. The medium texture detection device 30 is a device that detects a texture state of a surface Pb (hereinafter also referred to as a "lower surface" or a "detection surface") of a sheet-state medium P transported by a transport device (not illustrated) and coming into contact with a support surface 20a of a medium support unit 20 while being supported by the support surface 20a. In this example, a continuous sheet is exemplified as the medium P. In the case of a sheet, not a surface on the front side subjected to printing or the like (also referred to as a "front surface" or a "printing surface") but a surface on the rear side not subjected to printing or the like (also referred to as a "rear side surface" or a "non-printing surface") is preferably set as the detection surface Pb. In this way, in a case in which the medium texture detection device 30 is mounted on a printing apparatus, there is an advantage of easy mounting.

The medium texture detection device 30 includes a radiation optical system (also referred to as an "illumination optical system) 310, a light reception optical system 320, a light reception circuit 330, and a light reception control unit 340.

The radiation optical system 310 includes a light source 312 that emits non-coherent light and a light-guiding unit 314 that guides the non-coherent light emitted by the light source 312 as illumination light radiated to the lower surface Pb of the medium P passing through an opening 316 formed in the support surface 20a. As the light source 312, for example, a light source such as a light-emitting diode (LED) that emits non-coherent light with the wavelength by which the texture of the target medium P is easily detected can be used. For example, an LED that emits non-coherent light with a wavelength of an infrared region can be used. A light source such as an LED that emits non-coherent light with the wavelength of the visible region may be used. Here, non-coherent light with the wavelength of an infrared region is effective to detect a change in the surface of a medium according to the position of the medium as a change in the intensity of diffused/reflected light. Further, the influence of ambient light can be suppressed.

The light reception optical system 320 includes an optical fiber 322, a condensing lens 324, and a photosensor 326. The optical fiber 322 is disposed so that a light reception surface (incident surface) 322r comes into contact with the surface of the light-guiding unit 314 facing the lower surface Pb of the medium P on the opening 316. The light reception surface 322r is disposed near the lower surface Pb of the medium P via the light-guiding unit 314. The optical fiber 322 receives the diffused/reflected light of the light radiated to the medium P by the radiation optical system 310 through the light reception surface 322r and exits the diffused/reflected light from an exit surface 322o which is the other end surface. The radiation optical system 310 and the light reception optical system 320 are preferably configured such that the diffused/reflected light is received through the light reception surface 322r and mirror reflected light is not received. The condensing lens 324 condenses the light (diffused/reflected light) emitted from the exit surface 322o and radiates the light to the photosensor 326. The photosensor 326 converts the intensity of the received light into an electric signal (hereinafter also referred to as a "light reception signal"). As the photosensor 326, a photosensor (for example, a phototransistor or a photodiode) that has sensitivity in a wavelength region of the non-coherent light emitted by the light source 312 is used.

The radiation optical system 310 is fixed to the lower surface side of the support surface 20a so that a positional relation between the opening 316, and the light source 312 and the light-guiding unit 314 is changed and energy of the diffused/reflected light incident on the light reception surface 322r of the optical fiber 322 is not changed.

The energy of the diffused/reflected light incident on the light reception surface 322r of the optical fiber 322 decreases and a visual field (the size of a region of the detection surface of the diffused/reflected light which can be incident) on the light reception surface 322r increases as the light reception surface 322r is more away from the detection surface Pb. Accordingly, in order to reliably receive the diffused/reflected light through the light reception surface 322r, a gap (interval) between the light reception surface 322r and the detection surface Pb is preferably as narrow as possible to be constant in a range in which the radiation of the illumination light from the illumination optical system 310 to the opening 316 is not blocked.

Figure 2:
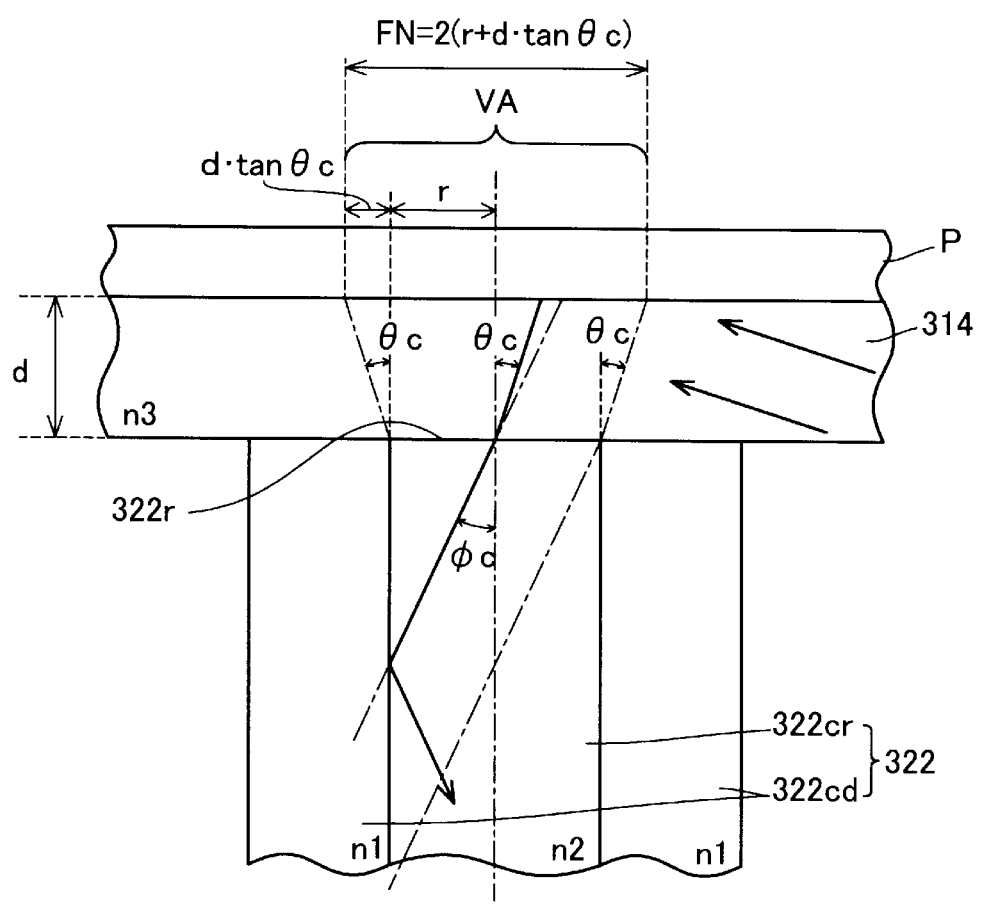
FIG. 2 is a diagram illustrating a relation between the size of a light reception surface of an optical fiber and the size of a visual field in which light can be received through the light reception surface.

FIG. 2 is a diagram illustrating a relation between the size of the light reception surface 322r of the optical fiber 322 and the size of the visual field in which light can be received through the light reception surface 322r. In FIG. 2, the light reception surface 322r of the optical fiber 322 and a portion of the light-guiding unit 314 between the medium P and the light reception surface 322r are expanded and illustrated.

Of the diffused/reflected light diffused and reflected from the medium P and incident on the light reception surface 322r of the core 322cr of the optical fiber 322, only the diffused/reflected light which repeatedly propagates on the interfaces between a core 322cr and a clad 322cd by total reflection and exits from the exit surface 322o (see FIG. 1) is received by the photosensor 326. An example indicated by a solid line in FIG. 2 indicates the diffused/reflected light incident at a maximum incidence angle θc in the diffused/reflected light incident on the light reception surface 322r to be totally reflected on the interface between the core 322cr and the clad 322cd of the optical fiber 322. Of the surface of the medium P, a region VA in which the diffused/reflected light incident on the light reception surface 322r to be totally reflected exits is a circular region which is larger than a circular region with a radius r of the core 322cr and has a radius of r+(d·tan θc). Here, d indicates a distance between the medium P and the light reception surface 322r of the optical fiber 322, that is, the thickness of the light-guiding unit 314. The region VA on the surface of the medium P corresponds to the visual field of the light reception optical system 320. The diameter of the visual field VA is referred to as a "visual field size FN". The visual size FN is given in Expression (1) below.

$$FN = 2(r + d \cdot \tan \theta c) \quad (1)$$

Here, a relation between the maximum incidence angle θc and the maximum refraction angle φc is expressed in Expression (2) below. Further, a total reflection condition in the core 322cr is expressed in Expression (3) below.

$$\sin \theta c = (n2/n3)\sin \phi c \quad (2)$$

$$\sin(90-\phi c) = n1/n2 \quad (3)$$

Here, n1 indicates a refractive index of the clad 322cd, n2 indicates a refractive index of the core 322cr, and n3 indicates a refractive index of the light-guiding unit 314.

The maximum refraction angle φc is obtained based on Expression (3) above, and then maximum incidence angle θc can be obtained based on the obtained maximum refraction angle φc and Expression (2) above. Then, the visual field size FN can be obtained using the obtained maximum incidence angle θc based on Expression (1). The radius r of the core 322cr of the optical fiber 322 corresponding to the desired visual field size FN can be obtained based on Expression (1), and thus an optical fiber to be used can be decided.

As the optical fiber 322, for example, an optical fiber in which the diameter of the core 322cr is 50 µm (r=25 µm), the refractive index n1 of the clad 322cd is 1.462, and the refractive index n2 of the core 322cr is 1.467 is assumed to be used. As the light-guiding unit 314, a light-guiding unit which is formed of a plastic material with the refractive index n1 of 1.500 and has a thickness d of 500 µm is assumed to be used. In this case, the visual field size FN is 106 µm.

The size of the light reception surface 322r of the optical fiber 322 is set according to a light-receivable visual field size in which a change in the texture state of the detection surface Pb can be used as a change in the diffused/reflected light. The visual field size and the size of the optical fiber will be further described below.

The light reception circuit 330 includes an amplifier 332 and an AD converter 334. The amplifier 332 amplifies a light reception signal S(x) of the diffused/reflected light from the photosensor 326 to match an input range of the AD converter 334. The AD converter 334 quantizes an analog intensity signal of the diffused/reflected light in order at a given sampling period is based on a sampling signal supplied from the light reception control unit 340 to convert the analog intensity signal into a digital light reception signal of the diffused/reflected light, and then outputs the digital intensity signal of the diffused/reflected light. The digital intensity signal of the diffused/reflected light includes output values of the photosensor 326 according to a position x of the medium P, that is, diffused/reflected light data DS(x) indicating the intensity of the diffused/reflected light in order.

The light reception control unit 340 supplies the sampling signal to the AD converter 334 and outputs the diffused/reflected light data DS(x) according to the position x at the sampling period is in order from the AD converter 334.

Figure 3:
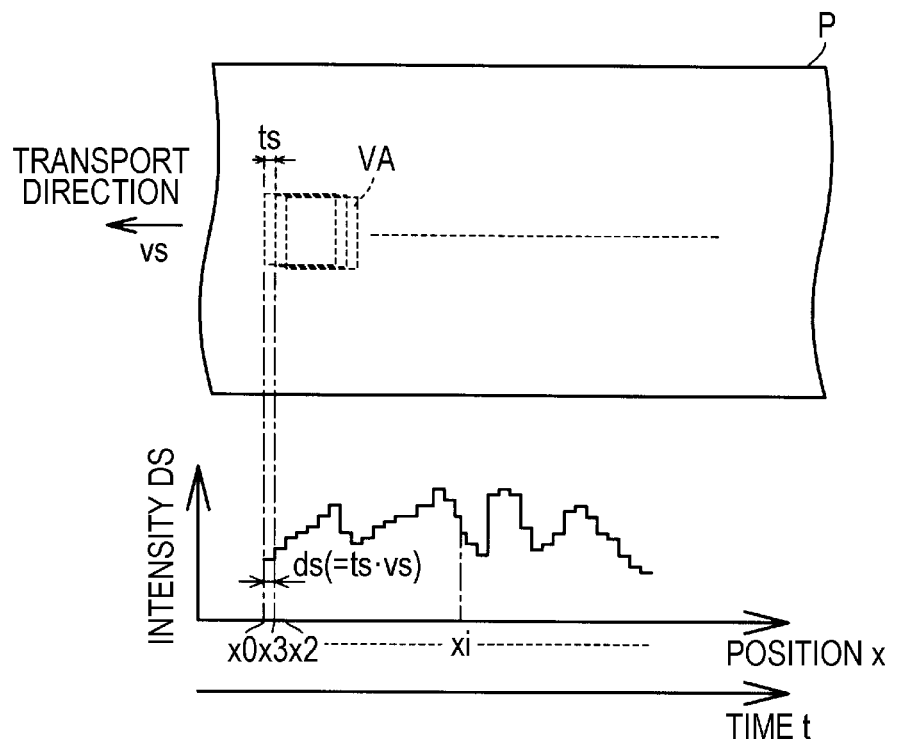
FIG. 3 is a diagram illustrating diffused/reflected light data output according to the position of a medium.

FIG. 3 is a diagram illustrating the diffused/reflected light data DS(x) output according to the position x of the medium P. Here, to facilitate illustration, the shape of the visual field VA of the light reception optical system 320 is drawn as a square. In practice, as described in FIG. 2, the visual field VA is circular. However, even when the visual field is considered to be a square with one side which has the same size as the diameter of the circular visual field, the function of the visual field VA is almost the same.

As the medium P transported at the transport speed vs is moved, the visual field VA of the preceding light reception optical system 320 is relatively deviated sequentially in an opposite direction to the transport direction of the medium P with reference to the medium P. At this time, sensor output values of the photosensor 326, that is, the diffused/reflected light data DS(x) indicating the intensity of the diffused/reflected light from the continuous sheet P corresponding to the visual field VA at the position x in order deviated at an interval ds (=ts·vs) of the medium P are output in order for each sampling period ts from the AD converter 334. Since the diffused/reflected light data output from the AD converter 334 is data output at each sampling period ts, the diffused/reflected light data DS(t) can be regarded as the diffused/reflected light data DS(t) output in order at the sampling period ts. The transport speed vs set in the transport device (not illustrated) may normally be set in the range of 0.1 µm/µs to 1 µm/µs. To match the transport speed vs, the sampling period ts may be set in a range from a value (for example, 1 µs) appropriate for the transport speed vs of 0.1 µm/s to a value (for example, 0.1 µs) appropriate for the transport speed vs of 1 µm/s.

As described above, the medium texture detection device 30 can detect the change in the texture state of the detection surface Pb changed according to the position of the medium P which is being transported as the change in the intensity of the diffused/reflected light.

Figure 4A:
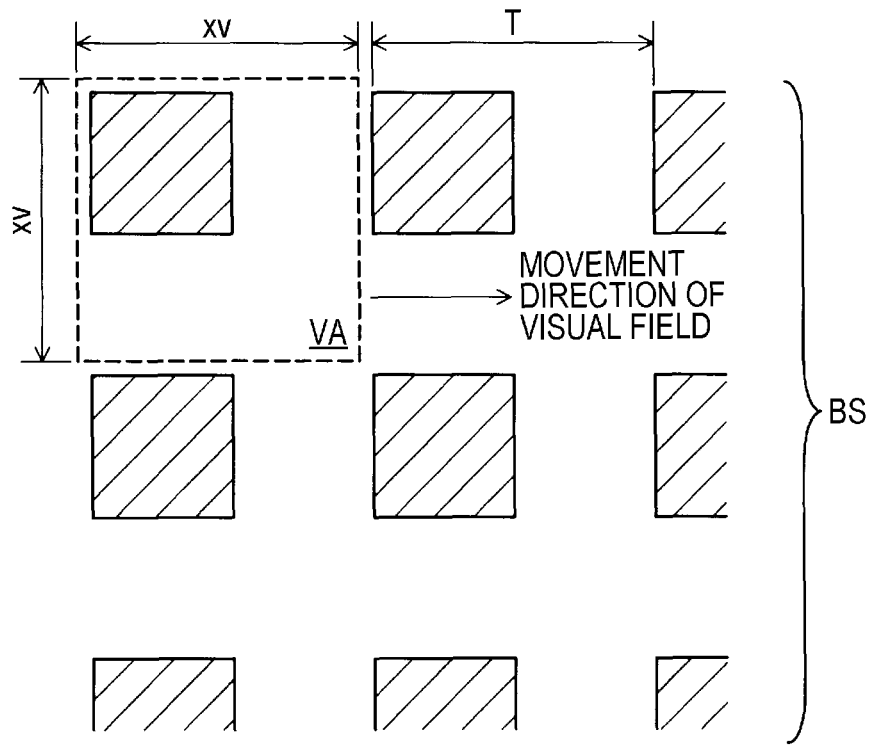
FIGS. 4A and 4B are diagrams illustrating a relation between the texture state of a detection surface of a sheet-shaped medium and diffused/reflected light.
Figure 4B:
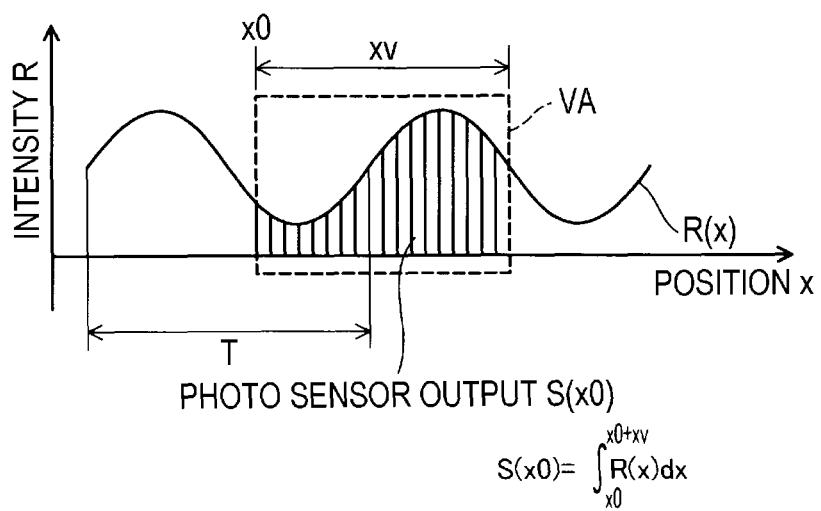

FIGS. 4A and 4B are diagrams illustrating a relation between the texture state of the detection surface Pb of the sheet-shaped medium P and the diffused/reflected light. The detection surface Pb of the medium P has a basic structure for generating a change in the intensity of the diffused/reflected light according to the position of the medium P. For example, in the case of a continuous sheet, generally, a sheet is configured such that dietary fiber (mainly, cellulose) with a length of about 0.25 mm to 50 mm and a thickness of 4 µm to 70 µm are amorphously woven and has a basic structure in which a period interval is in a range of about 1 µm to 500 µm. In FIG. 4A, to facilitate the description, a basic structure BS is illustrated as a structure in which simple unevenness of a period T is repeated (hatched square convex portion). The size of one size of the visual field VA is indicated as a square shape of xv. In a case in which the visual field VA is moved in a movement direction of the visual field, an intensity R(x) of the diffused/reflected light according to the position x of the visual field VA has a waveform repeatedly varying at the period T, as illustrated in FIG. 4B. An output S(x) of the photosensor 326 is a space integrated value of the intensity R(x) of the diffused/reflected light in the visual field VA. For example, an output X(x0) of the photosensor 326 at a position x0 is expressed in Expression (4) below in a case in which only the movement direction of the medium is focused on and a direction vertical to the movement direction of the medium is neglected for simplicity.

$$S(xO) = \int_{x0}^{x0+xv} R(x)dx \quad (4)$$

The lower limit of a visual field size xv is preferably set in the way to be described below. As expressed in Expression (4) above, the output of the photosensor 326 is a space integrated value of the intensity of the diffused/reflected light in the visual field VA. Therefore, the photosensor 326 can detect a change in the intensity R(x) of the diffused/reflected light finely as the visual field size xv is smaller than the period T of the basic structure BS. Accordingly, when an influence of disturbance or a speed limit by optical characteristics of the light reception optical system 320 and circuit characteristics of the light reception circuit 330 is neglected, there is basically no limit to the lower limit of the visual field size xv. In practice, however, as the visual field size xv decreases, the influence of disturbance or a speed limit by optical characteristics of the light reception optical system 320 and circuit characteristics of the light reception circuit 330 increases. Thus, the detection is considered to be difficult. In consideration of this problem, the visual field size xv is preferably set to be equal to or greater than 1/10 of the period T of the basic structure BS.

Figure 5:
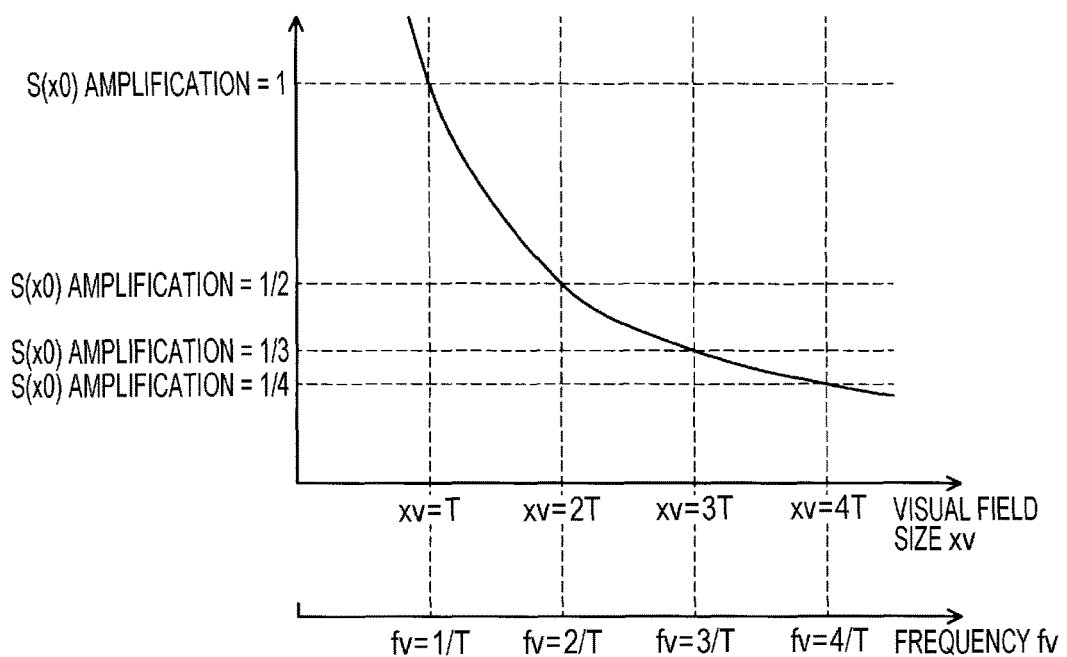
FIG. 5 is a diagram illustrating a relation between a visual field size and an output of a photosensor.

FIG. 5 is a graph illustrating an upper limit of the visual field size xv. FIG. 5 illustrates a relation between the visual field size xv and the output S(x) of the photosensor 326. An amplitude of the output S(x) decreases to 1/2, 1/3, 1/4, or the like in a case in which the visual field size xv is changed to 2, 3, 4 times or the like of the period T using an amplitude (=1) of the output S(x) as a standard in a case in which the period of the basic structure BS is fixed to the period T and the visual field size xv is the same as the period T. Similarly, an amplitude of the output S(x) decreases to 1/2, 1/3, 1/4, or the like in a case in which a space frequency fv is changed 2, 3, 4 time or the like using an amplitude (=1) of the output S(x) as a standard in a case in which the visual field size xv is fixed to the same value as the period T of the basic structure BS and the space frequency fv expressed by a reciprocal of the period of the basic structure BS is 1/T.

As illustrated in FIG. 4A, in a case in which the basic structure BS is a simple repetition structure, the period T can be detected when a gain of the amplifier 332 is adjusted in accordance with the magnitude of the amplitude of the output S(x). However, the actual basic structure BS is a combination structure of a plurality of structures with different periods or sizes and the output S(x) is an output in which a plurality of amplitudes at which the space frequencies are different mutually overlap. For this reason, when the visual field size xv is excessively large, the detection may be difficult due to an influence of S/N or an quantization error of the AD converter 334 in some cases. In a case in which the amplitude of the output S(x) obtained at the time of xv=T is regarded as a standard, it is desirable to obtain an amplitude of 1/8 or more and, more preferably, an amplitude of 1/4 or more. Accordingly, it is desirable to set the visual field size xv to 8 times or less of the period T of the basic structure BS and, more preferably, 4 times or less.

The period T of the basic structure BS is also referred to as "a size of the basic structure of the medium". The size of the basic structure BS corresponds to a period (space period) indicating a space frequency component that has a maximum real part among space frequency components included in the change in the diffused/reflected data DS(x) indicating the intensity of the diffused/reflected light according to the position of the medium P. The space frequency component can be obtained by performing fast Fourier transform (FFT) on the diffused/reflected light data DS(x) of the target medium.

In the embodiment, as described above, in regard to the medium (in this example, a continuous sheet) P in which the visual field size FN(=xv) is set to 106 μm and the size of the basic structure (the period of the basic structure) is set to 13.3 μm or more and, more preferably, 26.5 μm or more, it is possible to detect the change in the texture state of the detection surface of the medium changed according to the position as the change in the diffused/reflected light, using the optical fiber 322 including the core 322cr with diameter of 50 μm.

In the medium texture detection device 30 according to the embodiment, the radiation optical system 310 is configured as a radiation optical system with a simple structure including the light source 312 that emits the non-coherent light and the light-guiding unit 314 that guides the non-coherent light emitted by the light source 312 as the illumination light. The light reception optical system 320 is configured as a light reception optical system with a simple structure including the optical fiber 322, the condensing lens 324, and the photosensor 326. Accordingly, it is possible to resolve the problem of the increase in the size and cost of the imaging system device and the optical system device described in the related art. Thus, it is possible to detect the change in the texture state of the surface of the medium according to the position of the medium as the change in the intensity of the diffused/reflected light at a high speed with a simpler structure than in the related art.

B. Second Embodiment

Figure 6A:
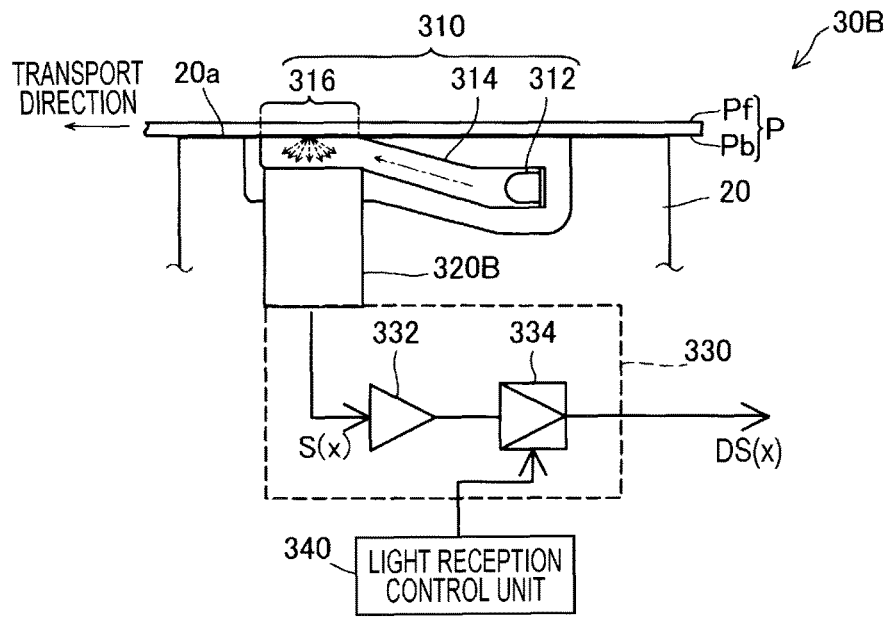
FIGS. 6A and 6B are schematic diagrams illustrating the configuration of a medium texture detection device according to a second embodiment.
Figure 6B:
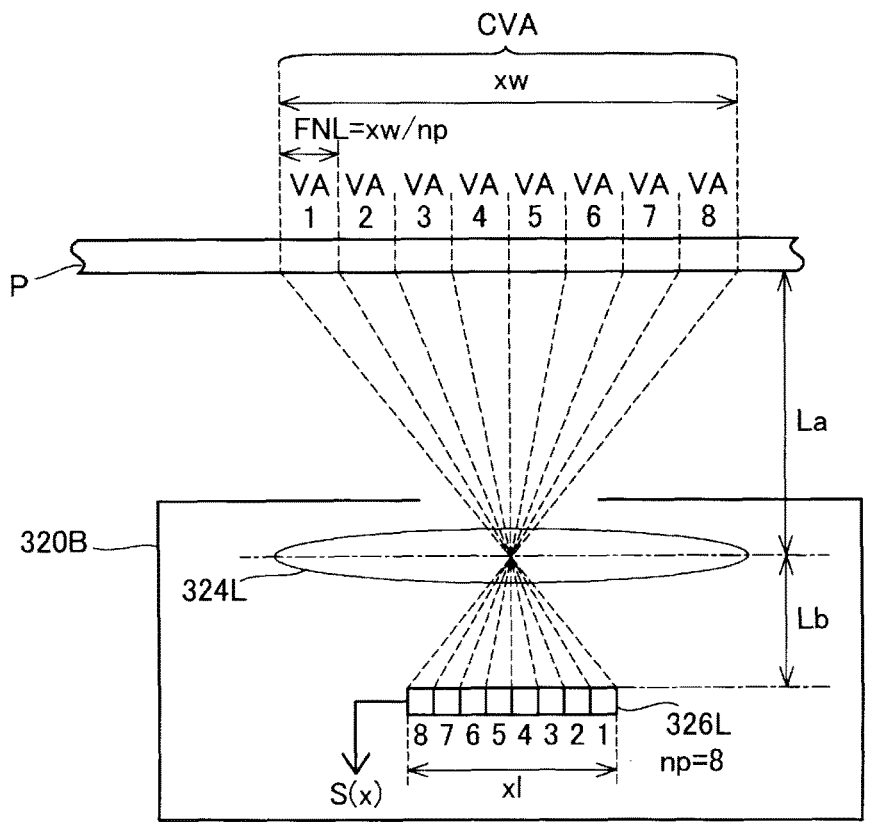

FIGS. 6A and 6B are schematic diagrams illustrating the configuration of a medium texture detection device 30B according to a second embodiment. As illustrated in FIG. 6A, the medium texture detection device 30B is a device in which the light reception optical system 320 of the medium texture detection device 30 (see FIG. 1) is substituted with a light reception optical system 320B. As expanded and illustrated in FIG. 6B, the light reception optical system 320B includes a line sensor 326L and a condensing lens 324L. The condensing lens 324L condenses the diffused/reflected light from an integration visual field CVA with an integration visual field size xw to radiate the diffused/reflected light to the line sensor 326L. The line sensor 326L is a sensor in which np light reception elements (in this example, np=8) converting light brightness and darkness into an electric signal are arranged in a row. A visual field size FNL of one light reception element is expressed in Expression (5) below.

$$FNL = xw/np \quad (5)$$

Here, a relation between a size xl of the line sensor 326L and the integration visual field size xw is expressed in Expression (6) below.

$$xw = xl \cdot m = xl \cdot (La/Lb) \quad (6)$$

Here, m indicates a magnification of the condensing lens 324L, La indicates a distance between the medium P and the condensing lens 324L, and Lb indicates a distance between the line sensor 326L and the condensing lens 324L.

An output from the individual light reception element of the line sensor 326L can be supplied as an output S(x) of the diffused/reflected light from the light reception optical system 320B to the amplifier 332, can be quantized by the AD converter 334, and can be output as digital diffused/reflected light data DS(x). In this way, the diffused/reflected light can be received with the visual field size FNL expressed in Expressions (5) and (6) above.

The visual field size FN in the light reception optical system 320 according to the first embodiment may not be set to a visual field size less than the core diameter of the optical fiber 322, as expressed in Expression (1) above. In a current situation, the core diameter of the optical fiber is generally 62.5 μm, 50 μm, or 9 to 10 μm. It is difficult to set the core diameter to a visual field size less than 5 μm. However, as indicated in Expressions (5) and (6) above, the visual field size FNL of the light reception optical system 320B according to the embodiment is a value obtained by dividing the integration visual field size xw decided by the magnification m (=La/Lb) of the condensing lens 324L and the size xl of the line sensor 326L by the number np of light reception elements of the line sensor 326L. Accordingly, by adjusting the magnification m of the condensing lens 324L and adjusting the integration visual field size, it is possible to set the visual field size of the light reception optical system 320B to a smaller size. Accordingly, it is possible to set the visual field size of the light reception optical system to a visual field size less than the core diameter of the optical fiber.

C. Third Embodiment

Figure 7:
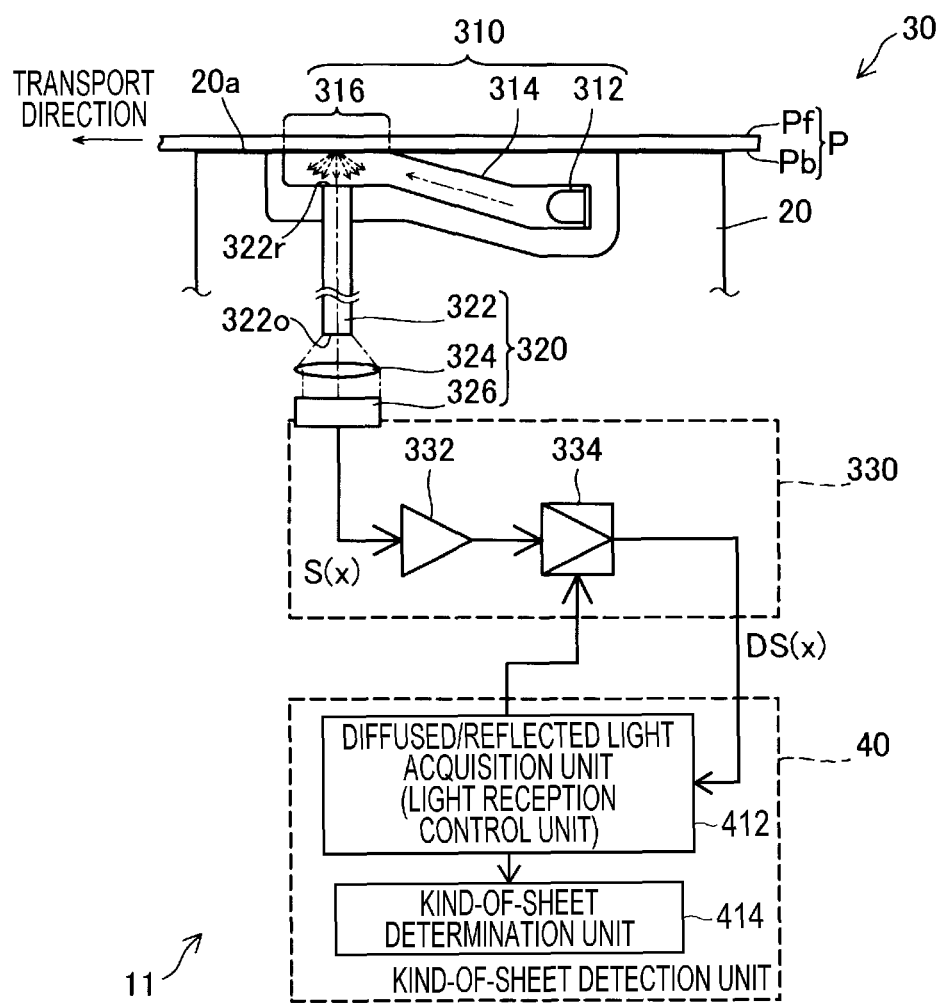
FIG. 7 is a schematic diagram illustrating the configuration of a kind-of-medium detection device to which the medium texture detection device is applied according to a third embodiment.

FIG. 7 is a schematic diagram illustrating the configuration of a kind-of-medium detection apparatus 11 to which the medium texture detection device 30 is applied according to a third embodiment. The kind-of-medium detection apparatus 11 is referred below to as a "kind-of-sheet detection apparatus 11" since the target medium P is set to a continuous sheet and the kind-of-sheet detection device that detects a kind of sheet is used as an example. The kind-of-sheet detection apparatus 11 includes the medium texture detection device 30 illustrated in FIG. 1 and a kind-of-sheet detection unit 40. A continuous sheet is exemplified as the measurement target sheet-shaped medium P of the medium texture detection device 30. The transport speed vs of the medium P is set to 0.1 μm/s and a temporal sampling period ts is set to 1 μs. In this case, a spatial sampling period ds, that is, a spatial resolution, is 0.1 μm.

The kind-of-sheet detection unit 40 is a control device configured as a computer system including a CPU, a memory such as a ROM or a RAM, and an interface (none of which is illustrated). The kind-of-sheet detection unit 40 functions as a diffused/reflected light acquisition unit 412 and a kind-of-sheet determination unit 414 by reading a program stored in a memory and executing the program.

The diffused/reflected light acquisition unit 412 supplies a sampling signal to the AD converter 334 of the light reception circuit 330, functions as a light reception control unit 340 (see FIG. 1) outputting the diffused/reflected light data DS(x) corresponding to a spatial sampling period ds (=0.1 μm) at the temporal sampling period is (=1 μs) in order from the AD converter 334, and acquires the diffused/reflected light data DS(x) output from the AD converter 334 in order.

The kind-of-sheet determination unit 414 determines a kind of sheet as the medium P based on the acquired diffused/reflected light data DS(x).

Figure 8A:
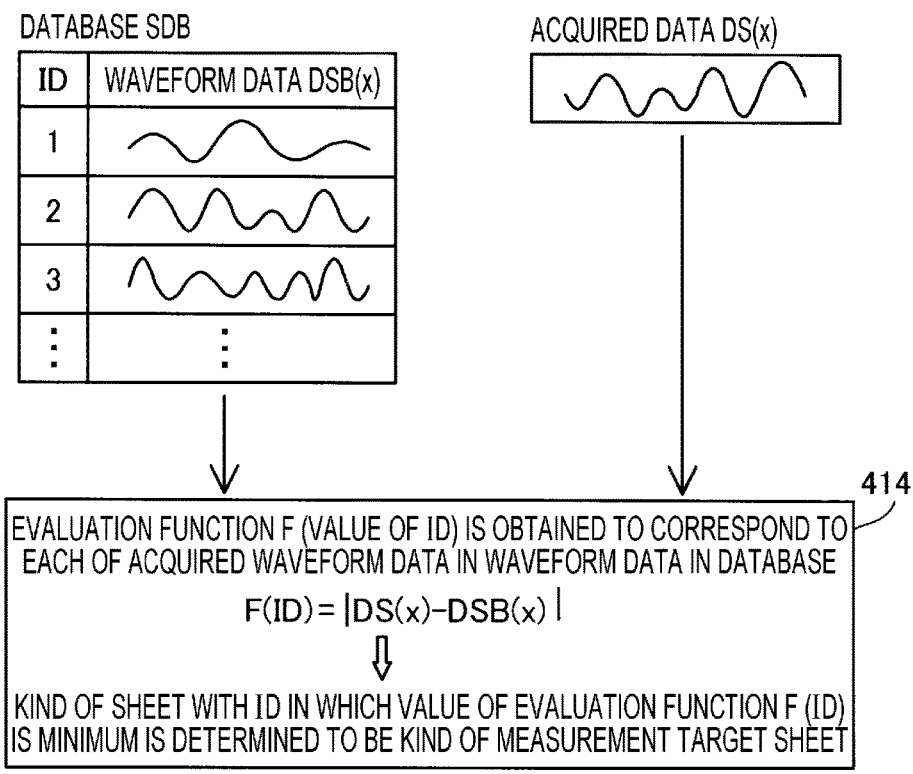
FIGS. 8A and 8B are diagrams illustrating kind-of-sheet determination by a kind-of-sheet determination unit.
Figure 8B:
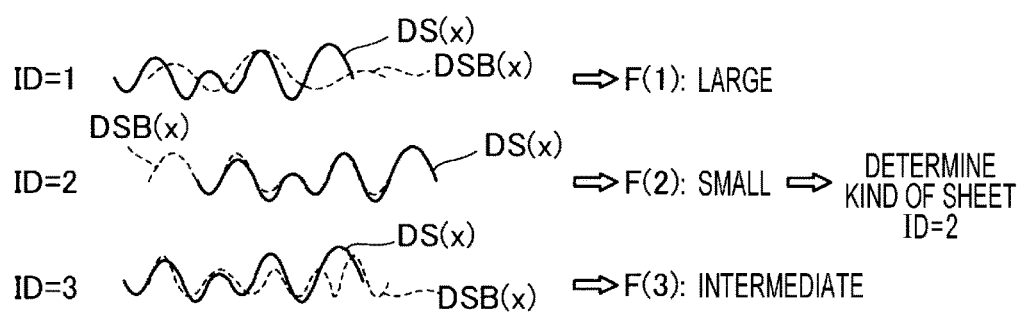

FIGS. 8A and 8B are diagrams illustrating kind-of-sheet determination by the kind-of-sheet determination unit 414. As illustrated in FIG. 8A, the kind-of-sheet determination unit 414 includes a database SDB. The database SDB stores an array of the diffused/reflected light data DSB(x) managed with an ID number indicating the kind of sheet. The database SDB of FIG. 8A shows an example in a case in which the array of the diffused/reflected light data DSB(x) corresponding to three kinds of sheets with IDs=1 to 3 is stored, to facilitate the illustration and description. However, the invention is not limited thereto. In the database SDB, the array of all the pieces of diffused/reflected light data DSB(x) corresponding to the number of kinds of supported sheets may be managed with ID numbers.

As illustrated in FIG. 8A, the kind-of-sheet determination unit 414 obtains an evaluation function value F(ID) expressed in the following Expression (7) for the acquired waveform data (the array of the pieces of diffused/reflected light data DS(x)) to correspond to acquired waveform data in regard to waveform data (the array of the pieces of diffused/reflected light data DSB(x)) of ID numbers stored in the database SDB.

$$F(ID)=\Sigma|DS(x)-DSB(x)| \quad (7)$$

Here, when phases, amplitudes, or offsets are different between the diffused/reflected light data DSB(x) of the database and the acquired diffused/reflected light data DS(x), results of the evaluation function value F(ID) are considerably different. Accordingly, it is desirable to adjust the phase, the amplitude, or the offset of the acquired diffused/reflected light data DS(x) in the array of the diffused/reflected light data DSB(x) with one ID number and obtain the minimum evaluation function value F(ID) for the diffused/reflected data DSB(x) with the ID number.

Then, the kind of sheet of the ID of the minimum evaluation function value F(ID) among the obtained evaluation function values F(ID) is determined to be the kind of measurement target medium P in regard to the pieces of diffused/reflected light data DSB(x) with all the ID numbers. For example, as illustrated in FIG. 8B, ID=1 is set to F(1): large, ID=2 is set to F(2): small, and ID=3 is set to F(3): intermediate. In this case, the kind of sheet of the measurement target medium P is determined to be a kind of sheet of ID=2.

As described above, the kind-of-sheet detection device 11 to which the medium texture detection device 30 is applied can detect the kind of sheet of the measurement target medium P from the diffused/reflected light data DS(x) changed according to the position x of the medium P detected by the medium texture detection device 30.

D. Fourth Embodiment

Figure 9:
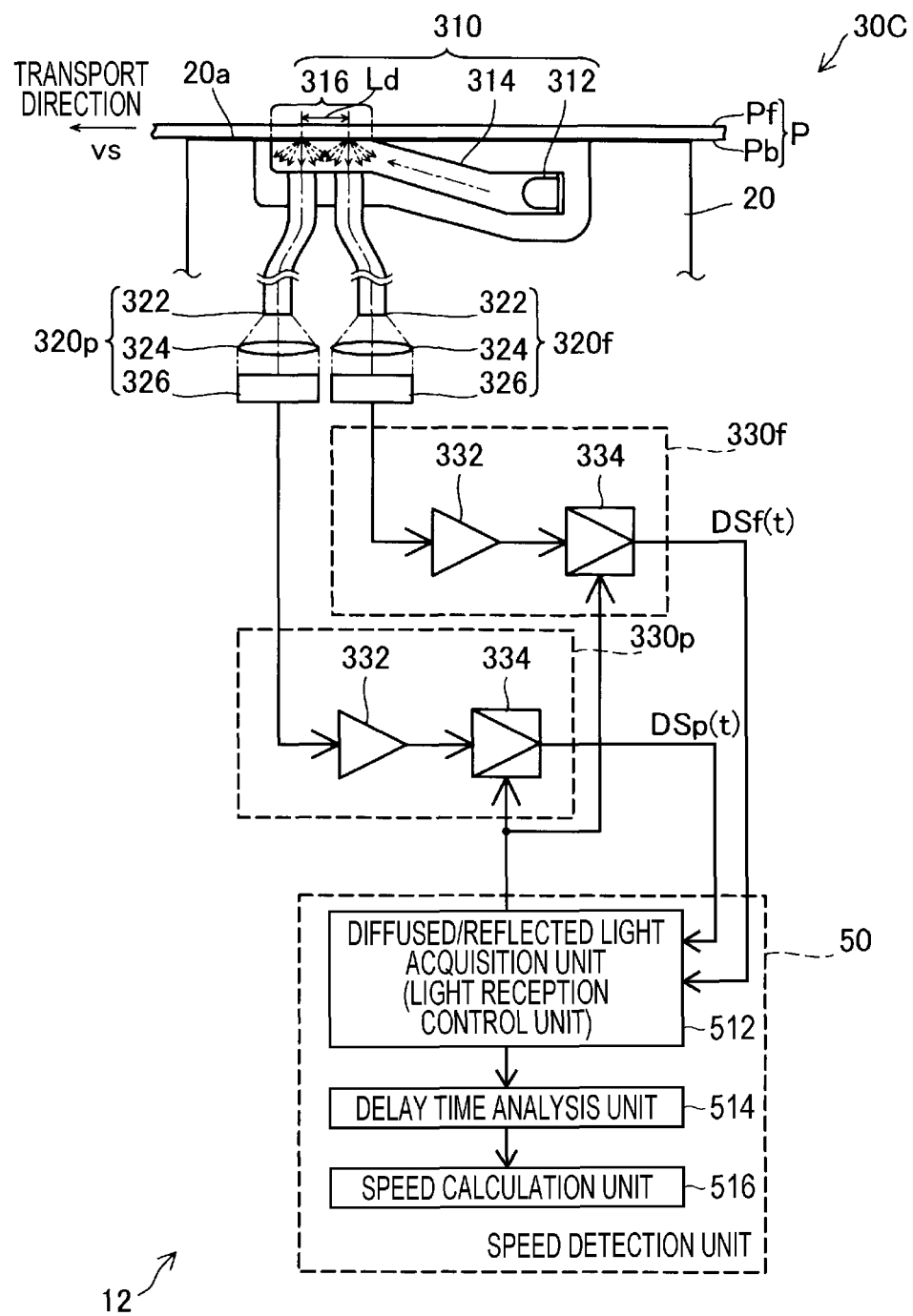
FIG. 9 is a schematic diagram illustrating the configuration of a medium speed detection device to which a medium texture detection device is applied according to a fourth embodiment.

FIG. 9 a schematic diagram illustrating the configuration of a medium speed detection device 12 to which a medium texture detection device 30C is applied according to a fourth embodiment. The medium speed detection device 12 includes the medium texture detection device 30C and a speed detection unit 50.

The medium texture detection device 30C includes two light reception optical systems 320$f$ and 320$p$ arranged in the transport direction of the medium P and two light reception circuits 330$f$ and 330$p$ corresponding to the two light reception optical systems 320$f$ and 320$p$. The two light reception optical systems 320$f$ and 320$p$ and the two light reception circuits 330$f$ and 330$p$ have the same configurations as the light reception optical system 320 and the light reception circuit 330 of the medium texture detection device 30 (see FIG. 1). The optical fiber 322 of the preceding first light reception optical system 320$f$ in the transport direction and the optical fiber 322 of the following second light reception optical system 320$p$ in the transport direction are disposed on the light-guiding unit 314 at a given interval Ld in the transport direction. In this example, the interval Ld is assumed to be 100 μm.

The preceding first light reception optical system 320$f$ and first light reception circuit 330$f$ and the following second light reception optical system 320$p$ and second light reception circuit 330$p$ each receive the diffused/reflected light from the medium P and output the pieces of diffused/reflected light data DSf(t) and DSp(t) at the temporal sampling period ts. Here, the disposition positions of the first light reception optical system 320$f$ and the optical fiber 322 and the disposition positions of the second light reception optical system 320$p$ and the optical fiber 322 are distant by the given time Ld in the transport direction, as described above. Therefore, the temporal sampling period ts is preferably set to a value by which the diffused/reflected light data sufficiently expressing a change in the diffused/reflected light occurring while the medium P is moved by the interval Ld with high precision can be acquired. For example, when the number of samplings is set in a range of 100 to 1000 at the interval Ld of 100 μm in a range of the transport speed vs of 0.1 μm/μs to 1 μm/μs, the sampling period ts is preferably set to any value in the range of 0.1 μs to 1 μs. In this example, ts=1 μs is set.

The diffused/reflected light data DSp(t) received by the following second light reception optical system 320p is assumed to b later by a delay time Δt expressed in Expression (8) below than the diffused/reflected light data DSf(t) received by the preceding first light reception optical system 320f.

$$\Delta t = Ld/vs \tag{8}$$

Here, Ld indicates an interval between the disposition position of the optical fiber 322 of the first light reception optical system 320f and the disposition position of the optical fiber 322 of the second light reception optical system 320p, and vs indicates the transport speed (movement speed) of the medium P.

Based on Expression (8) above, the transport speed vs is expressed in Expression (9) below.

$$vs = Ld/\Delta t \tag{9}$$

Accordingly, when the delay time Δt is known, the transport speed vs can be said to be calculated using the delay time Δt as a movement time. A method of obtaining the delay time Δt will be described below.

The speed detection unit 50 is a control device configured as a computer system including a CPU, a memory such as a ROM or a RAM, and an interface (none of which is illustrated). The speed detection unit 50 functions as a diffused/reflected light acquisition unit 512, a delay time analysis unit 514, and a speed calculation unit 516 by reading a program stored in a memory and executing the program.

The diffused/reflected light acquisition unit 512 supplies sampling signals to the AD converters 334 of the first light reception circuit 330f and the second light reception circuit 330p, functions as a light reception control unit outputting the pieces of diffused/reflected light data DSf(t) and DSp(t) in order at the time temporal sampling period is from the AD converters 334, and acquires the pieces of diffused/reflected light data DSf(t) and DSp(t) output from the AD converters 334 in order.

Figure 10:
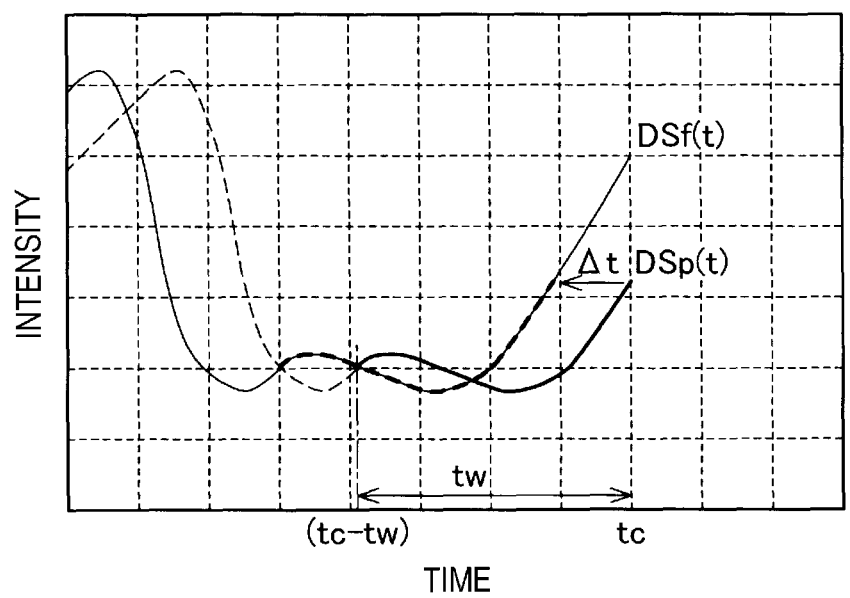
FIG. 10 is a graph illustrating a relation between preceding first diffused/reflected light data and following second diffused/reflected light data.

FIG. 10 is a graph illustrating a relation between the preceding first diffused/reflected light data DSf(t) and the following second diffused/reflected light data DSp(t). The delay time analysis unit 514 (see FIG. 9) takes a correlation between the diffused/reflected light data DSp(tc−tw) to DSp(tc) and the preceding first diffused/reflected light data DSf(t) in a range previous by a period tw from a current time tc of the following second diffused/reflected light data DSp(t). Then, the time difference Δt between the following second diffused/reflected light data DSp(tc−tw) to DSp(tc) and preceding first diffused/reflected light data DSf(tc−Δt) to DSf(tc−tw−Δt) (which is data in a range indicated by the dotted line in the drawing) correlated with the following second diffused/reflected light data DSp(tc−tw) to DSp(tc) is obtained as a delay time. Specifically, for example, the delay time Δt at which a correlation value R(Δt) expressed in Expression (10) below is minimum may be searched for.

$$R(\Delta t) = \int_{tc-tw}^{tc} S[DSf(t-\Delta t) - DSb(t)] \cdot dt \tag{10}$$

Here, tc indicates a current time and tw indicates a period in which the correlation is taken and a period in which the number of samplings sufficient at the sampling period is =1 μs, for example, the number of samplings of 100 points or more, is ensured. In this example, tw=100 μs is set.

The speed calculation unit 516 (see FIG. 9) calculates the transport speed vs from Expression (11) below.

$$vs = Ld/tm \tag{11}$$

Here, Ld indicates an interval (100 μm) between the disposition position of the optical fiber 322 of the first light reception optical system 320f and the disposition position of the optical fiber 322 of the second light reception optical system 320p, and tm indicates a movement time in which the medium P is moved by the interval Ld and is the delay time Δt in which and the correlation value R(Δt) obtained by the delay time analysis unit 514 is minimum.

As described above, the medium speed detection device 12 to which the medium texture detection device 30C is applied can detect the transport speed (movement speed) vs of the medium P from the pieces of diffused/reflected light data DSf(t) and DSp(t) varying according to the position of the medium P detected by the medium texture detection device 30C.

E. Modification Examples

The invention is not limited to the foregoing examples or embodiments, can be embodied in various aspects within the scope of the invention without departing from the gist of the invention. For example, the invention can be modified as follows.

(1) The foregoing medium texture detection devices 30, 30B, and 30C have described as examples of the configuration using the radiation optical system 310 including the light source 312 that emits the non-coherent light and the light-guiding unit 314 that guides the non-coherent light emitted by the light source 312 as the illumination light. However, the invention is not limited thereto. The radiation optical system is, for example, a radiation optical system that has a structure disposed so that non-coherent light is radiated as illumination light to a sheet-shaped medium and diffused/reflected light of reflected light reflected from the medium is received by a light reception optical system, as in a dark field illumination optical system.

(2) The foregoing medium texture detection devices 30 and 30C have described as examples of the configurations in which the light reception optical systems 320, 320f, and 320p including the optical fiber 322, the condensing lens 324, and the photosensor 326 are used. Further, the medium texture detection device 30B has been described as an example of the configuration in which the light reception optical system 320B including the condensing lens 324L and the line sensor 326L is used. However, the invention is not limited thereto. The light reception unit may be a light reception optical system that has a structure with a visual field in which the diffused/reflected light changed according to the texture of a medium is received. For example, a light reception optical system including a pinhole and a photosensor may also be used.

(3) The medium texture detection device is not limited to the configuration including one light reception optical system. As in the medium texture detection device 30C used in the medium speed detection device 12 in FIG. 9, a configuration including a plurality of light reception optical systems in the transport direction or a configuration including a plurality of light reception optical systems in a direction vertical to the transport direction may be used. A change in a texture state of the surface of a medium according to the position of the medium as a change in the intensity of diffused/reflected light can be detected in each of the plurality of light reception optical systems.

(4) The sheet-shaped medium is not limited to a continuous sheet, but may be a single sheet. Further, a film made of resin, a composite film of resin and metal (laminated film), a woven fabric, a non-woven fabric, a ceramic sheet, or the like may be used. However, a transparent medium, a black medium, and a metal medium are excluded.

The invention is not limited to the embodiments, the examples, and the modification examples described above, but can be realized in various configuration within the scope of the invention without departing from the gist of the invention. For example, technical characteristics of the embodiments, the examples, and the modification examples corresponding to the technical characteristics of the aspects described in SUMMARY can be appropriately replaced or combined to resolve some or all of the above-described problems or to achieve some or all of the above-described advantages. If the technical characteristics are not described as essentials in the present specification, the technical characteristics can be appropriately deleted.

This application claims priority under 35 U.S.C. § 119 to Japanese Patent Application No. 2015-171825, filed Sep. 1, 2015. The entire disclosure of Japanese Patent Application No. 2015-171825 is hereby incorporated herein by reference.

What is claimed is:

1. A medium texture detection device comprising:
 a radiation optical system that radiates non-coherent light to a non-printing surface Pb of a sheet-shaped medium which is being transported, wherein the non-printing surface Pb is on an underside of the sheet-shaped medium; and
 a light reception optical system that receives diffused/reflected light of the non-coherent light from the medium,
 wherein a surface of the medium has a basic structure for making a change in an intensity of the diffused/reflected light according to a position of the medium in a transport direction of the medium, and
 wherein a visual field of the light reception optical system is set to be equal to or greater than $1/10$ times and equal to or less than 4 times of a size of the basic structure.

2. The medium texture detection device according to claim 1, wherein the size of the basic structure is a space period indicating a space frequency component that has a maximum real part among space frequency components included in the change in the intensity of the diffused/reflected light.

3. The medium texture detection device according to claim 1, wherein the non-coherent light is light with a wavelength of an infrared region.

4. The medium texture detection device according to claim 1, wherein the radiation optical system includes
 a light source that emits the non-coherent light, and
 a light-guiding unit that guides the non-coherent light to the medium, and wherein the light reception optical system includes
 an optical fiber that receives the diffused/reflected light from the medium through an incidence surface which is one end surface as a light reception surface and exits the diffused/reflected light from an exit surface which is the other end surface,
 a photosensor that receives the diffused/reflected light emitted from the exit surface and outputs an electric signal according to an intensity of the received diffused/reflected light, and
 a condensing lens that condenses the diffused/reflected light emitted from the exit surface of the optical fiber toward the photosensor.

* * * * *